United States Patent [19]

Sugimoto

[11] 4,328,207
[45] May 4, 1982

[54] PROCESS FOR PREPARING MOUSE INTERFERON

[75] Inventor: Kaname Sugimoto, Okayama, Japan

[73] Assignee: Ken Hayashibara, Okayama, Japan

[21] Appl. No.: 107,557

[22] Filed: Dec. 27, 1979

[51] Int. Cl.$^3$ .................. A61K 45/02; A61K 39/00
[52] U.S. Cl. .................................. 424/85; 435/68; 435/811
[58] Field of Search .................... 424/85; 435/68, 811

[56] References Cited

U.S. PATENT DOCUMENTS 4,276,282  6/1981  Sugimoto ............................. 424/85

FOREIGN PATENT DOCUMENTS 54-98307  8/1979  Japan .

OTHER PUBLICATIONS

Chemical Abstracts, vol. 81, p. 391, Abst. No. 167513d, Sans et al., "Production of Mouse Interferon with High Liters in a Large-Scale Suspension Culture", 1974.
Chemical Abstracts, vol. 79, p. 298, Abst. No. 90455k, Tovey et al., "Production of Interferon by Chemostat Cultures of Mouse LS-Cells Grown in Chemically Defined, Protein Free Medium", 1973.
Chemical Abstracts, vol. 74, p. 190, Abst. No. 21415g, Khesin et al., "Cytological Study of a Peritoneal Exudate from Mice in Course of Interferon Production In Vitro", 1971.
Chemical Abstracts, vol. 89, p. 382, Abst. No. 88763x, Zaretsku et al., "Matrix Synthesis of Mouse Interferon in Heterological Systems In Vitro and In Vivo", 1978.
Miyoshi et al., Cancer, vol. 40, No. 6, pp. 2999-3003, 1977.
Dianzani, F. et al., Advances in Experimental Medicine and Biology, vol. 110, pp. 119-131, 1978.
De Maeyer-Guinard, J., "Mouse Leukemia: Depression of Serum Interferon Production", Science, (Sep. 1972), pp. 797-799.
Thompson, J. S. et al., "Heterologous Transplantation of Mouse Tumors into the Newborn Albino Rat", Cancer Research, vol. 20, pp. 1365-1371, (1960).
Solov'ev, V. D. et al., "Interferon Theory and Applications", Plenum Press, New York -London, 1973, pp. 3-18.

*Primary Examiner*—Blondel Hazel
*Attorney, Agent, or Firm*—Browdy and Neimark

[57] ABSTRACT

The present invention relates to a process which is easily applicable for industrial production of mouse interferon.

Particularly, the present invention relates to a process based on the discovery that a large amount and high activity of mouse interferon is obtained by transplanting established mouse tumor cells to other warm-blooded animal body or inoculating the cells in a culture medium charged in a filter-membrane-interposed diffusion chamber which is designed and fitted up to or in the animal body so that its nutrient body fluid feeds the cells, multiplying the transplanted or inoculated cells in the warm-blooded animal body or the diffusion chamber utilizing said body fluid, and exposing the multiplied cells to the action of interferon inducer in vitro or in vivo.

3 Claims, No Drawings

PROCESS FOR PREPARING MOUSE INTERFERON

DETAILED DESCRIPTION OF THE INVENTION

The present invention relates to a process for preparing mouse interferon.

As reported in "Science", vol. 177, pp. 797–799 (1972), it is well documented that normal mouse cells induce mouse interferon of relatively high activities, while mouse tumor cells induce mouse interferon of considerably low activities. Normal mouse cells are, however, not proper for large-scale production of mouse interferon because they multiply much slower than mouse tumor cells.

Envisaging the utilization of high multiplication rates of mouse tumor cells, the present inventors performed studies for large-scale production of mouse interferon with said cells.

The efforts resulted in the discovery that a large amount of and high-titred mouse interferon was not obtainable by inoculating and culturing established mouse tumor cells in a culture medium in vitro, or transplanting and multiplying the cells in mouse body utilizing its nutrient body fluid, but easily obtainable by transplanting said cells in other warm-blooded animal body or inoculating the cells in a culture medium charged in a filter-membrane-interposed diffusion chamber which is designed and fitted up to or in the animal body so that its nutrient body fluid feeds the cells, multiplying the transplanted or inoculated cells in the warm-blooded animal body or the diffusion chamber utilizing said body fluid, exposing the multiplied cells to the action of interferon inducer in vitro or in vivo to induce a high-titred mouse interferon, and purifying and separating the induced mouse interferon.

The process according to the present invention differs from the conventional processes in which the cells are multiplied in vitro, and has advantages that it requires no or much less nutrient medium supplemented with expensive serum, that the maintenance and control of the conditions during the multiplication of the established mouse tumor cell are much easier, and that higher-titred mouse interferon is easily obtainable.

More particularly, in the process according to the present invention, established mouse tumor cells can be easily multiplied in other warm-blooded animal body utilizing the body fluid by either transplanting said cells therein, or embedding or connecting in or to the animal body with a diffusion chamber charged with a culture medium suspended with said cells, while feeding the animal in the usual way.

As compared with the conventional processes in which established mouse tumor cells are multiplied in vitro, the process according to the invention in which the cells are multiplied utilizing nutrient body fluid from the warm-blooded animal body has further features that the multiplication of the cells is steadier, the multiplication rate is higher, and that the yield of the induced interferon per cell is much higher.

Any established mouse tumor cell may be used as far as it can multiply when transplanted in other warm-blooded animal body; for example L 5178 Y cell, SM 36 cell, L 1210 cell, FAC-C cell, T 3 cell, M 1 cell, OUMS-2 cell, JTC-11 cell, ELD cell and Sarcoma 180 cell, as reported in "Protein, Nucleic Acid and Enzyme", vol. 20, no. 6, pp. 616–643 (1975). Particularly, mouse lymphoblastoid cell lines such as L 5178 Y cell, L 1210 cell, OUMS-2 cell and JTC-11 cell are preferable because of their high multiplication rates and the attainment of high activities of the induced interferon.

Any warm-blooded laboratory animal can be used in the invention as far as the transplanted established mouse tumor cells can multiply therein; for example birds such as chicken and pigeon, and mammalians such as dog, cat, monkey, goat, pig, bovine, rabbit, horse, guinea pig, rat and hamster.

Since transplantation of mouse tumor cells in the above-mentioned animal body tends to cause undesirable immunoreactions, animals in the most immature state, namely, egg, fetus, embryo, or new-born or infant animal, should be chosen to depress the immunoreactions as much as possible.

Prior to transplantation of the cell, the animal may be pretreated, for example either by irradiating with about 200–600 rem of X-ray or $\gamma$-ray, or with antiserum or an immunosuppressive agent, to depress the immunoreactions.

Instead of transplanting and multiplying established mouse tumor cells in animal body, the cells can be inoculated and multiplied in a nutrient of other warm-blooded animal body in a conventional-type diffusion chamber which is embedded, for example intraperitoneally, and devised to allow the cells to utilize said body fluid.

The chambers which are usable in the invention can be of various shapes and sizes and should be interposed with filter membranes, for example membrane filter, ultra-filter and hollow fiber, to prevent the leakage of the cells. Particularly, the chambers with interposed filter membranes of pore sizes of about $10^{-7}$ to $10^{-5}$ m are preferable.

In addition, established mouse tumor cells, if necessary, can be multiplied in a nutrient body fluid circulating through the diffusion chamber which is connected to a certain part of the animal body and placed, for example on the surface of the animal body, to allow the animal to feed the cells with its nutrient body fluid.

Furthermore, designing and connecting the diffusion chamber so that it can be disconnected periodically from the animal body and the cells multiply through the whole life of the animal without any unnecessary sacrifice of animal, the animal will further increase the yield of the multiplied cells per animal.

Furthermore, the process using the above-mentioned diffusion chamber has an additional feature besides the multiplied mouse tumor cells can be easily harvested because there is no direct contact of the cell with the animal cell, that various warm-blooded animals can be used without any pretreatment to depress their immunoreactions because of their lower possibilities of causing the immunoreactions.

As to the induction of mouse interferon, any method can be employed as far as it induce interferon in the multiplied living mouse cells.

The multiplied cells can be exposed in vivo to the action of interferon inducer wherein they developed, or exposed in vitro to the action of interferon inducer after isolation of them.

Particularly, when mouse tumor cells are multiplied in a diffusion chamber, the exposure of the multiplied cells to the action of interferon inducer in or out of the chamber induces mouse interferon.

TABLE II-continued

| Phenethylether Derivative | Organoleptic Properties of Detergent Composition |
|---|---|
| 1-methallyl phenethylether produced according to Example III. | |

The foregoing compositions are added to an aqueous laundrying bath at concentrations of 0.20% (weight) each at a temperature of 55° C., water hardness 7 grains per gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics have pleasant aromas as described in Table II above and are also rather long-lasting (about 3 days).

EXAMPLE XV

Preparation of Cosmetic Powder Compositions

Cosmetic powders are prepared by admixing in a ball mill, 100 grams of talcum powder with 0.25 grams of the phenethylether derivative as set forth in Table III below. The resulting cosmetic powders have aromas as set forth in Table III below which are very long-lasting.

TABLE III

| Phenethylether Derivative | Organoleptic Properties of Cosmetic Powder |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

EXAMPLE XVI

Perfumed Liquid Detergent

Concentrated liquid detergents (lysine sale of n-dodecylbenzene sulfonic acid as more specifically described in U.S. Pat. No. 3,948,818 issued on Apr. 6, 1976) with aromas as set forth in Table IV below are prepared containing 0.10%, 0.15%, 0.20% and 0.25% of the phenethylether derivatives as set forth in Table IV below. They are prepared by adding and homogeneously admixing the appropriate quantities of phenethylether derivatives in the liquid detergent. The detergents all possess intense and long-lasting aromas as set forth in Table IV below.

TABLE IV

| Phenethylether Derivative | Detergent Aroma Profile |
|---|---|
| 1,3-dimthyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

EXAMPLE XVII

Preparation of Colognes and Handkerchief Perfumes

Phenethylether derivatives as set forth in Table V below are incorporated into colognes at concentrations of 2.0%, 2.5%, 3.0%, 3.5%, 4.0% and 4.5% in 80%, 85%, 90% and 95% aqueous food grade ethanol; and into handkerchief perfumes at concentrations of 15%, 20%, 25% and 30% (in 80%, 90% and 95% aqueous ethanol solutions). Distinctive aromas as set forth in Table V below which are very long-lasting on dry-out (44 hours) are imparted to the colognes and to the handkerchief perfumes at the various above levels indicated.

TABLE V

| Phenethylether Derivative | Organoleptic Properties of Colognes and Handkerchief Perfumes |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methylallyl phenethylether produced according to Example III. | A green, floral aroma. |

What is claimed is:

1. A method of attracting and destroying *Lasioderma serricorne* (F.) comprising applying to an area contaminated with said *Lasioderma serricorne* (F.) at least one phenethylether defined according to the structure:

[chemical structure: phenyl ring with -CH2-O-R substituent]

wherein R is isopropyl or 1,3-dimethylbutye, said attractant being applied to said area in an amount sufficient to attract said *Lasioderma serricorne* (F.).

* * * * *

The dogs were fed in the usual way, and about 4 weeks later the chambers were removed from the dogs.

The cell concentration of the chambers was about $4 \times 10^9$ cells per ml which was about $10^2$ to $10^3$ times or more higher than that attained in vitro on a nutrient medium in a $CO_2$ incubator.

The cells were treated and the induced mouse interferon was partially purified and concentrated, similarly as described in Example 1. Then, the mouse interferon-containing concentrate was freeze-dried into powder.

The interferon activity of the powder was about 50,000,000 units per dog.

EXAMPLE 6

Established mouse tumor cells of JTC-11 cells were transplanted in the allantoic cavities of embryonated eggs which had been pre-incubated at 37° C. for 5 days, and then were incubated for an additional 5 days.

The eggs were opened and the multiplied mouse tumor cells were harvested. Then, the cells were treated and the induced mouse interferon was partially purified and concentrated, similarly as described in Example 1.

The interferon activity of the concentrate was about 700,000 units per 10 embryonated eggs.

What we claim is:

1. In the process for producing mouse specific interferon comprising cultivating established mouse cells, exposing the resultant cells to the action of an interferon inducer to induce interferon, and collecting and purifying the interferon, the improvement wherein the established mouse cells are established mouse lymphoblastoid cell lines selected from the group consisting of L 5178 Y cell, L 1210 cell, OUMS-2 cell and JTC-11 cell, and wherein said cultivating step comprises transplanting the established mouse tumor cells into another non-mouse warm-blooded laboratory animal body, and wherein said exposing step is in vivo or in vitro.

2. A process according to claim 1 in which the non-mouse warm-blooded laboratory animal is a mammalian.

3. A process according to claim 1, wherein said non-mouse warm-blooded laboratory animal is a bird, dog, cat, monkey, goat, pig, bovine, rabbit, horse, guinea pig, rat or hamster.

* * * * *